United States Patent [19]

Abdel-Mottaleb

[11] Patent Number: 5,579,360
[45] Date of Patent: Nov. 26, 1996

[54] MASS DETECTION BY COMPUTER USING DIGITAL MAMMOGRAMS OF THE SAME BREAST TAKEN FROM DIFFERENT VIEWING DIRECTIONS

[75] Inventor: Mohamed Abdel-Mottaleb, Ossining, N.Y.

[73] Assignee: Philips Electronics North America Corporation, New York, N.Y.

[21] Appl. No.: 367,023

[22] Filed: Dec. 30, 1994

[51] Int. Cl.$^6$ ............................................. A61B 6/00
[52] U.S. Cl. .................................. 378/37; 382/132
[58] Field of Search ................ 378/37, 210; 382/130, 382/131, 132, 133

[56] References Cited

U.S. PATENT DOCUMENTS

| | | | |
|---|---|---|---|
| 5,133,020 | 7/1992 | Giger et al. | 382/6 |
| 5,212,637 | 5/1993 | Saxena | 364/413.26 |
| 5,426,685 | 6/1995 | Pellegrino et al. | 378/87 |

OTHER PUBLICATIONS

"Computerized Detection Of Masses In Digital Mammograms: Automated Alignment Of Breast Images And Its Effect On Bilateral–Subtraction Technique", Fang–Fang Yin et al, Med. Phys. vol. 21, No. 3, Mar. 1994, pp. 445–452.

Primary Examiner—David P. Porta
Assistant Examiner—David Vernon Bruce
Attorney, Agent, or Firm—Jack D. Slobod

[57] ABSTRACT

Two digital radiologic images taken from different viewing directions of a same region, notably a mammogram study of the same breast, are automatically processed by a computer to identify suspect masses by producing processed mammogram images in which suspect spots, the skinline and the nipple are marked or enhanced. Candidate suspect spots are initially identified by individually processing each mammogram image separately. Then characteristics of the candidate spots identified in the mammogram images taken from different viewing directions are compared to eliminate false positives. The characteristics compared include position of the spots relative to the explicitly detected nipple, and their size, shape, brightness and brightness variance. The candidate spots are separately identified by thresholding the breast region of the mammogram at 20 or more threshold levels determined from a histogram of the image to discriminate spots, and classifying the spots by size, shape and variance in intensity of the pixels comprising the spot. Overlaps are resolved after the comparison between views.

18 Claims, 5 Drawing Sheets

MASS DETECTION BY COMPUTER USING DIGITAL MAMMOGRAMS OF THE SAME BREAST TAKEN FROM DIFFERENT VIEWING DIRECTIONS

RELATED APPLICTION

This application is a continuation-in-part of a U.S. patent application by the same inventor which was filed on Jul. 14, 1994 as Ser. No. 08/274,939 entitled "Mass Detection in Digital X-ray Images Using Multiple Thresholds to Discriminate Spots". This application is also related in subject mater to the application by the same inventor as this application and filed simultaneously therewith entitled "Automatic Segmentation, Skinline and Nipple Detection in Digital Mammograms". The later application is expressly incorporated herein by reference.

BACKGROUND OF THE INVENTION

1. Field of the Invention

The present invention relates generally to methods of and systems for computer aided diagnosis or screening of digital mammogram images. In its more particular aspects, in relates to identification of spots that may correspond suspect areas in a manner which in order to reduce the incidence of false positives includes a comparison of mammogram images of the same breast taken from different viewing or projection directions.

2. Description of the Related Art

A method of this general type is known from U.S. Pat. No. 5,133,020, particularly FIGS. 15(a) and (b) thereof and the associated discussion which describes identifying an "island" in one view of a breast as a false positive when there is no corresponding "island" at the same depth in a view of the same breast from a different viewing direction. The depth appears to be determined in each view perpendicular to a line in a mammogram coordinate direction which is tangent to a detected skinline.

Typically mammogram studies are taken from at least two viewing directions selected from the head-to-toe viewing direction known as cranio-caudal (CC), the side-to-side viewing directions known as medio-lateral (ML) or lateral-medial (ML) and the viewing direction which is generally at a 45° angle between head-to-toe and side-to-side known as oblique (OB).

Early detection of breast cancer, the second most frequently occurring cancer in women, can significantly increase the patient's chances of survival. Such early detection requires periodic screening mammograms which are read by radiologists or mammographers for the presence of masses (also referred to as lesions or nodules) and clusters of microcalcifications as signs of malignancy. Both the number of mammograms to be interpreted and the difficulty of identifying these not easily recognizable signs of malignancy obscured by intensity gradations due to other tissue motivate developments in Computer-Aided Diagnosis of Mammograms (CADM) to at least automatically mark or enhance features of interest, including suspect areas, in images displayed on a monitor or printed on film or other media for visual interpretation by the mammographer.

Digital mammograms suitable for computer-aided diagnosis may be obtained by scanning film taken by conventional X-ray mammography or by utilizing other X-ray detector types that produce electronic image signals that may be directly digitized without the necessity of producing a film intermediate. These detector types include X-ray image intensifier/camera chain, photostimuable phosphor plate/laser readout (see U.S. Pat. No. 4,236,078), and selenium plate/electrometer readout technologies. Such technologies are progressing in their spatial resolution and contrast sensitivities achieved and the latter two, particularly, may soon find widespread use for mammographic applications.

One of the early steps in a CADM system is to segment a mammogram image into foreground (corresponding to the breast) and background (corresponding to the external surround of the breast). This segmentation reduces the amount of further processing because extraneous pixels belonging to the background are removed from further consideration. Also, the boundary contour or border between the foreground and the background, theoretically at the skinline, is ascertained. While the nipple is an important landmark, unless the nipple was marked by a metal bead, it is very difficult to detect in the mammogram. Often, it is not visualized in profile due to patient positioning or rolling over of the skin.

Next, a search for masses within the area segmented as corresponding to the breast may be accomplished by analyzing the size and shape of spots, sometimes referred to as "blobs" or "islands", that are discriminated by thresholding the mammogram at one or a few intensity levels. For example, in U.S. Pat. No. 5,212,637, a search for masses in different intensity ranges utilizes a calculated initial threshold value which threshold value is incremented no more than three times. "Blobs" produced by thresholding the mammogram at the initial or at an incremented threshold value, which correspond to regions having a sufficient prominence in intensity with respect to their immediate surround are classified as "potentially malignant" based on their size and shape, i.e. area, circularity, and eccentricity.

In U.S. Pat. No. 4,907,156, "islands" are produced by thresholding a difference image determined from a digital X-ray image. The threshold level is successively decreased which, in general, causes the islands to grow. At each threshold level, the shape and size of the islands are analyzed. An island is classified as a nodule based upon its effective diameter and circularity.

The aforementioned methods using a single mammogram view may yield an unacceptable number of false positive results, particularly when attempting to increase their sensitivity to a degree that false negatives are virtually eliminated. While there is the potential to use information from two different views of the same breast to reduce or eliminate these false positives as suggested in the aforementioned U.S. Pat. No. 5,133,020, in practice it is difficult to correlate positions in different views because the skinline alone is not a sufficient reference to determine if suspect masses in both views correspond to each other in position. Further, if a plurality of threshold values are used to discriminate spots in each view, the prior art does not suggest how any overlapping spots in each view should be compared.

SUMMARY OF THE INVENTION

It is a general object of the present invention to provide a method and apparatus for computer aided diagnosis of suspect spots in digital mammogram images which substantially reduces or eliminates the incidence of false positive results by comparing mammograms of the same breast taken from different viewing directions to enable correlation of the positions of the suspect spots in the different views relative to an explicitly determined reference point corresponding to the nipple;

It is a further object of the present invention that the positions of suspect spots in two different views of the same breast be one of several measured characteristics which are compared to reduce or eliminate false positives;

It is yet another object of the present invention that the incidence of false negatives also be substantially reduced or eliminated by using a large number of relevant threshold levels to discriminate suspect spots in each of the two views individually prior to comparing the characteristics of the spots discriminated in the two views.

Briefly, these and other objects are satisfied by, in each of two views taken from different viewing directions, individually identifying candidate suspect spots and then comparing characteristics of the identified spots including a position measure relative to an anatomical reference point corresponding to the nipple to determine whether spots in the different views correspond to each other. In addition to the position measure, measures of size, shape, intensity variance and brightness are compared. Any candidate suspect spot in a view for which no corresponding candidate suspect spot is found in the other view is labelled as a false positive and not reported or highlighted as suspect.

The reference point corresponding to the nipple is located in each view individually after the mammogram is segmented into breast and background and the skinline is detected. A search along the segment of the detected skinline and into the area segmented as the breast is performed to locate the nipple based on an increased intensity in the breast due to structure associated with the nipple. The measure of position is computed for each identified candidate suspect shot by determining a central point or center of mass of the spot with respect to the reference point corresponding to the nipple. The measure is preferably a distance component, referred to herein as "depth", along a line passing through the point corresponding to the nipple and a point determined from the shape of the breast in the particular view. The latter point is preferably the center of mass of the breast. Alternatively, a Euclidian distance between the center of the spot and the reference point may be used as the measure of position.

Prior to the aforementioned comparison between two different views of the same breast, suspect spots are identified in the two mammogram views individually using thresholding at many threshold levels. This separate processing of the two views proceeds by first forming a histogram of the gray levels of pixels in a foreground mammogram (a mammogram view whose background has been removed from consideration by the segmentation and skinline detection) to determine a relevant interval of gray levels for the multiple thresholds. The foreground mammogram is thresholded at each gray level in the interval. Typically, in an 8 bit (256 gray level) image, the relevant interval contains at least 20 and typically more than 50 different gray levels. The image resulting from each thresholding operation is separately analyzed to determine connected regions or spots, and to classify which connected regions are suspect. At each gray level in the interval, pixels that belong to a suspect connected region are marked. This marking process is cumulative, since, after thresholding at each gray level in the interval, all pixels belonging to a suspect connected region in a binary image produced at any threshold level in the interval have been marked.

The determination of which connected regions are suspect is done by forming measures of their respective size, shape and intensity variance or uniformity. Each connected region whose measures all meet predetermined criteria are designated as suspect. The inclusion of an intensity variance or uniformity criterion is because a typical suspect mass appears to have a relatively uniform intensity throughout its area.

Thresholding at each gray level in a relatively large interval of relevant levels, tends to produce a 100% sensitivity in identifying suspect masses. The maintenance of a low rate of false positives is aided by the inclusion of the criterion requiring that the pixels of a connected region have low variance or high uniformity in intensity. This criterion, among other things, prevents substantially hollow connected regions from being designated as suspect.

Because the spots discriminated at different threshold levels may at least partially overlap each other, it is necessary after the view comparison procedure to eliminate redundancies from among the identified pairs of spots which are found to have similar feature vectors by determining overlaps and marking only the largest of the overlapping spots.

BRIEF DESCRIPTION OF THE DRAWING

Other objects, features and advantages of the invention will become apparent upon perusal of the following detailed description when taken in conjunction with the appended drawing, wherein.

DETAILED DESCRIPTION OF THE PREFERRED EMBODIMENTS

Figure 1:
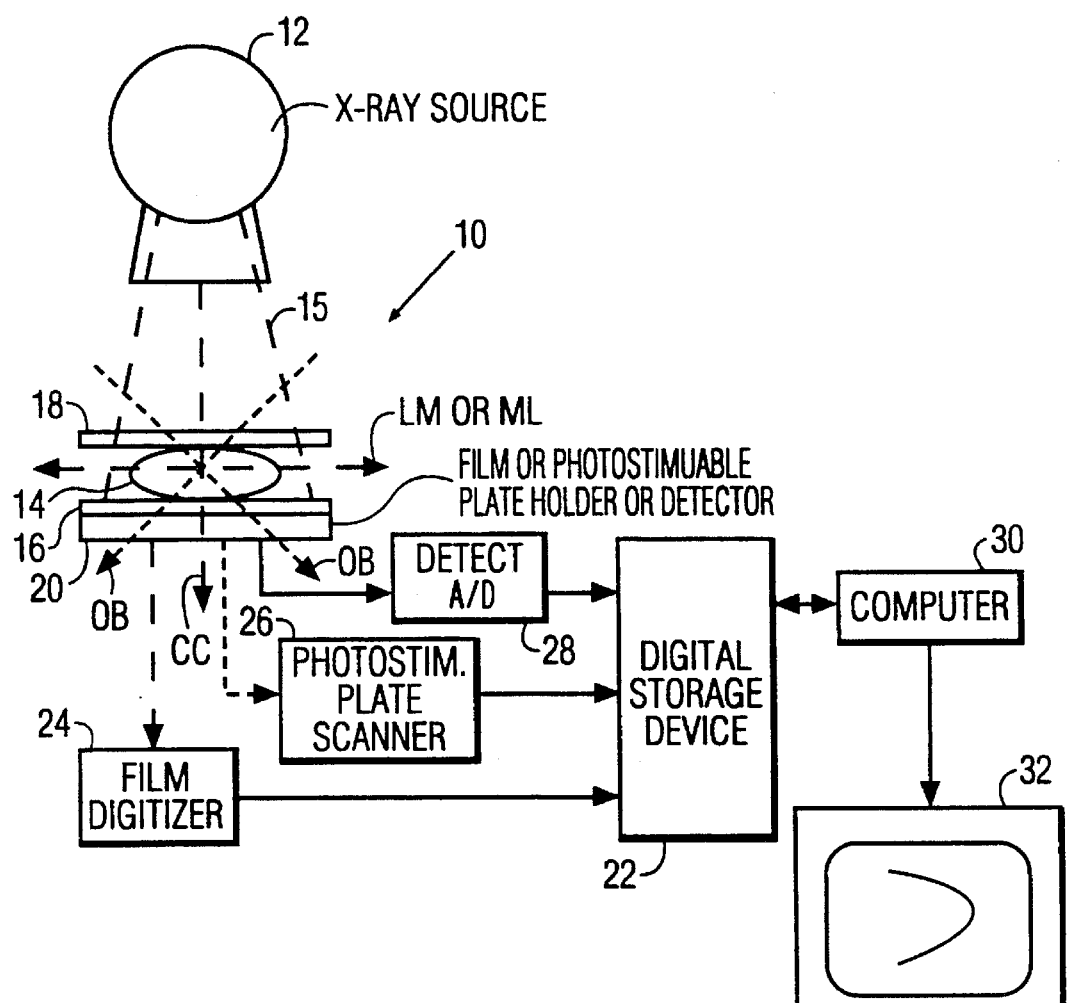
FIG. 1 is a schematic diagram of a computer-aided system in accordance with the invention for taking and processing mammograms.

Referring first to FIG. 1, there is shown a computer-aided mammography system 10, with its mammogram taking parts arranged for a cranio-caudal (CC) view, including an X-ray source 12 directed to irradiate a breast 14 of a standing patient with an X-ray beam 15. The breast 14 is received and compressed between generally planar lower and upper members 16, 18, using a predetermined compression force or weight. Below lower member 16 is a two-dimensional X-ray detector means 20 for detecting within a rectangular field of pixels, the X-ray radiation passing through breast 14 and its immediate external surround. X-ray detector means 22 is alternatively a film or a photostimuable phosphor image plate received in a holder, or a selenium plate/electrometer readout detector. An X-ray image intensifier/camera chain is also a suitable detector means. The X-ray source 12, plates 14 and 16 and detector means 20 may be rotated as a unit about transverse axis A to receive and irradiate breast 14 along any of the viewing directions labelled in FIG. 1 as CC (cranio-caudal), LM or ML (latero-medial or medial-lateral) and OB (oblique). In practice, mammogram studies are taken from at least two of these viewing directions.

Whichever detector means 20 type is used, ultimately there is a two-dimensional array of digital pixels for each viewing direction, each representing a mammogram X-ray projection image, stored as an image file in a digital storage device 22 which may comprise a RAM, hard disk, magneto-optical disk, WORM drive, or other digital storage means. When film is used, it is developed and then scanned in a digitizer 24. Today, films may be digitized to 100 micron spatial resolution, yielding typical images ranging in size from 1672×2380 to 2344×3016 pixels, each up to 12 bit intensity resolution. When a photostimuable plate is used, it is scanned by a laser in scanner 26 yielding a similar image size and typically 10 bit intensity resolution. Lastly, when a detector such as a selenium plate/electrometer readout device is utilized, it directly produces analog electrical signals that are converted to digital form by its analog digital to converter 28.

The study comprising two-dimensional arrays of digital pixels stored in device 22, representing mammograms taken from two or more viewing directions are processed by computer workstation 30 to mark or enhance features of interest which correspond to each other in the different mammogram views, including any identified suspect masses or clusters of microcalcifications, and display either one or both of the resultant processed mammograms on display device 32, such as a CRT monitor.

Figure 2A:
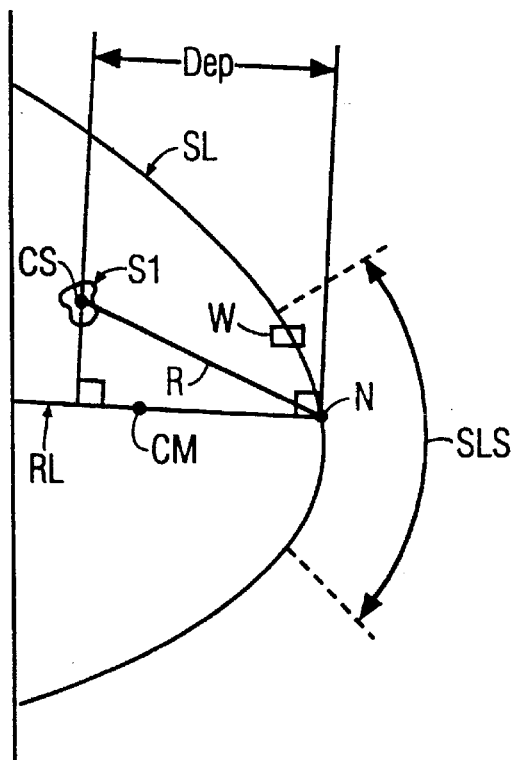
FIGS. 2A and 2B generally illustrate cranio-caudal (CC) and oblique (OB) mammogram views, respectively, of the same breast illustrating spot positions to be compared.
Figure 2B:
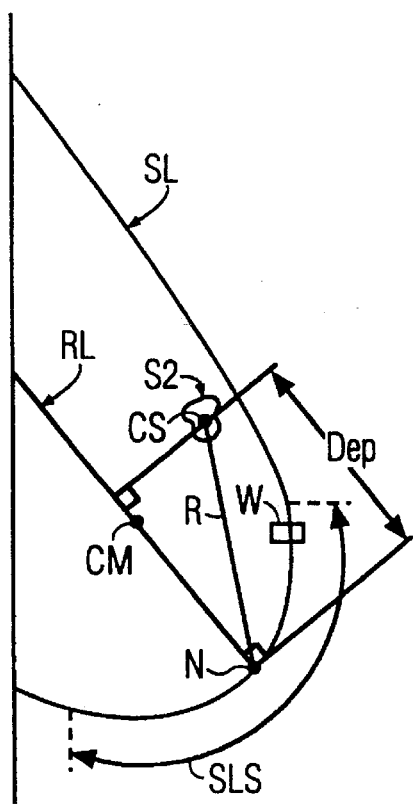

As will become apparent as the discussion proceeds, the two or more viewing directions enable comparison of position and other characteristics of spots discriminated individually in the separate views to determine if they correspond to a same actual spot in the breast of the patient. FIGS. 2A and 2B generally illustrate cranio-caudal (CC) and oblique (OB) mammogram views, respectively, of the same breast and indicate the required automatic measurement of the position of spot S1 in the cranio-caudal view and of spot S2 in the oblique view. In particular, a reference line RL is determined in each view passing through a center of mass CM of the breast and a detected reference point N corresponding to the nipple which lies on a detected skinline SL. The position measurement is taken as a depth Dep which is the distance component between the reference point N and a center of mass CS of the applicable spot along reference line RL. The explicit detection of the reference point N corresponding to the nipple and the determination of the reference line RL provide a frame of reference for correct comparison of positions in views taken from different viewing directions. Alternatively, the distance measurement may be simply the Euclidian distance R between the reference point N and the spot center CS, in which case it is unnecessary to determine the reference line RL. The coordinates of each spot center CS are conveniently estimated as the average of the coordinates of the pixels making up the spot. The center of mass CM of the breast is determined as a centroid of the pixels making up the breast.

Figure 3:
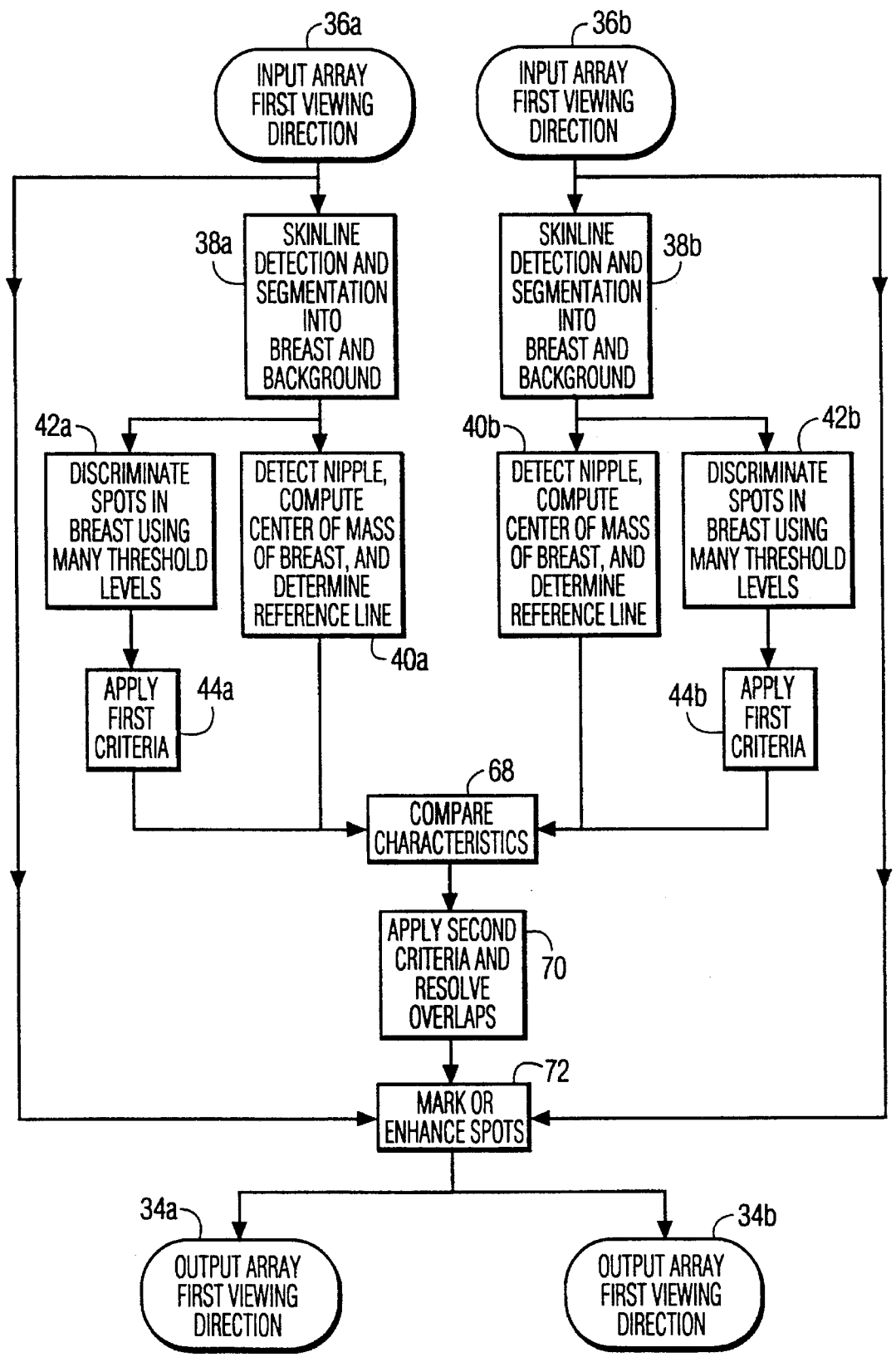
FIG. 3 is a flow chart indicating an overview of the processing performed by a computer in FIG. 1 including portions for individually processing mammograms taken from different viewing directions to discriminate spots followed by comparison of the results of the results of the individual processing.

With reference to the flow chart of FIG. 3, an overview of the procedure by which workstation 30 produces output arrays 34a and 34b corresponding to enhanced mammogram images in at least first and second different viewing directions suitable for display on monitor 32 (or for printing on film or other media) will now be given. As a preliminary step which is not specifically illustrated, each stored mammogram image in the study is preferably reduced in resolution, spatially by a suitable median filter, and/or in amplitude by truncation, to an image on the order of 500,000 to 2,500,000 pixels and 8-bit to 10-bit intensity resolution consistent with the spatial and gray scale resolution of the monitor. It has been found experimentally that good results are obtained with resolution reduced images having square pixels with 0.4 micron sides and 256 gray levels. The mammogram images from at least two different viewing directions as suitably reduced in spatial and/or amplitude resolution form the input arrays 36a, 36b from first and second viewing directions which are input to the procedure illustrated in FIG. 3.

In steps 38a, 38b the input arrays 36a, 36b are respectively individually segmented into foreground, corresponding to the breast, and background, corresponding to the external surround of the breast and the skinline SL (see FIGS. 2A and 2B) is detected in the course of this segmentation. The segmentation allows background to be eliminated from the search for features of interest, such as masses or clusters of microcalcifications, to be marked or enhanced. The segmentation may be performed by the method described in U.S. patent application Ser. No. 08/175,805, filed Dec. 30, 1993, entitled "Automatic Segmentation and Skinline Detection in Digital Mammograms", which is assigned to the same assignee as the present application and is hereby incorporated herein by reference. Preferably, however, the segmentation and detection of skinline SL (see also FIGS. 2a and 2B) is done in accordance with the method described in the application by the same inventor as this application and filed simultaneously therewith entitled "Automatic Segmentation, Skinline and Nipple Detection in Digital Mammograms", which as previously noted is expressly incorporated herein by reference. In addition to the explicitly detected skinline, a background removed image is conveniently formed in which all background pixels have been set to black.

In steps 40a and 40b, the reference point N corresponding to the nipple is expressly detected automatically, preferably in accordance with the procedure described in the aforementioned simultaneously filed application. With reference to FIGS. 2A and 2B, this method involves isolating a high curvature segment SLS of the skinline SL and moving a small rectangular window W along each point in the segment to search for a bright (high attenuation) area within the breast below the nipple caused by subcutaneous parenchymal tissue. Window W is directed into the breast and is preferably two pixels high by eight pixels wide (i.e. 0.8×3.2 microns) from a point on the skinline segment SLS. At each position of the window, the average (or total) of the intensities in window W is computed. The point on the skinline at which the window W has the greatest average (or total) intensity is chosen to be the detected reference point corresponding to the nipple.

Further, in steps 42A and 42B, spots are discriminated using many threshold levels in the region segmented as the breast and thereafter in blocks 44a and 44b first criteria are applied to determine candidate suspect spots. The procedures therefor are more fully detailed in the flowchart of FIG. 4, which begin by in step 46 determining a histogram of the gray values of the pixels in the breast and then from the histogram determining a relevant interval of gray levels for thresholding.

Figure 5:
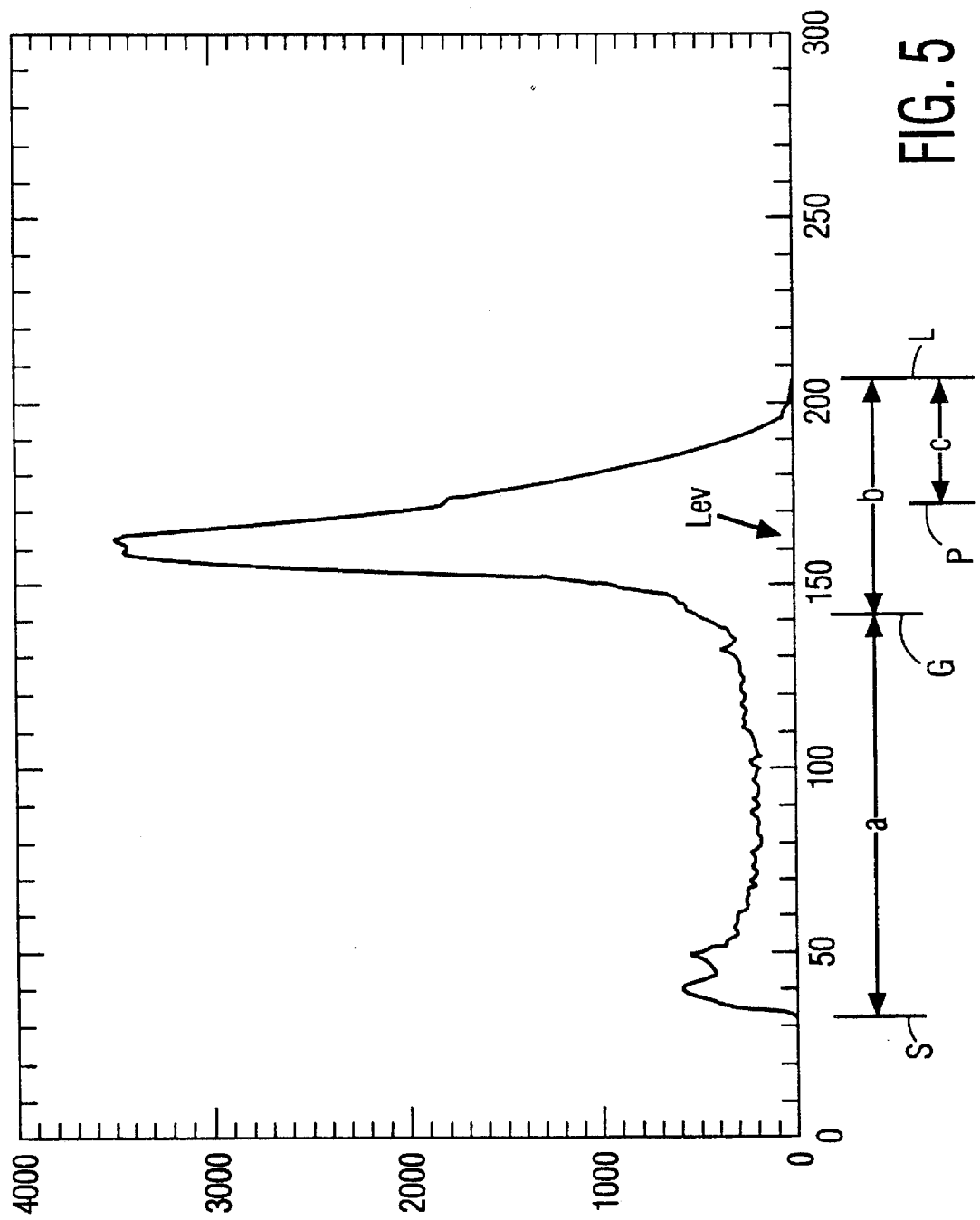
FIG. 5 is a histogram of the gray values of the pixels of a mammogram after background removal which is used in conjunction with the discrimination of spots in the individual views as shown in the flow chart of FIG. 4.

A typical histogram of the pixels in the breast is shown in FIG. 5 and is seen to be subdividable into an interval "a" from the smallest gray level S in the histogram to a gray level G, which interval corresponds to the skin, and a narrower interval "b" from level G to the largest gray level L in the histogram, which interval corresponds to the interior of the breast. Interval "a" has a substantially low number of pixels at each gray level while interval "b" has a relatively high peak with steep sides. The interval "b" is chosen as the relevant interval of gray levels for thresholding. Gray level G is chosen such that interval "b" twice the interval "c" between gray level L and the gray level P at the peak of the histogram.

In accordance with the invention, each gray level "Lev" in interval "b" is used as a threshold. Typically, in a 256 gray level image interval "b" contains at least 20 twenty gray levels, and often more than 50. Conveniently, these gray levels are successively used as a threshold level in either smallest to largest, or largest to smallest, order. In any event, a current threshold level is set at the first gray level interval "b" in the order.

Figure 4:
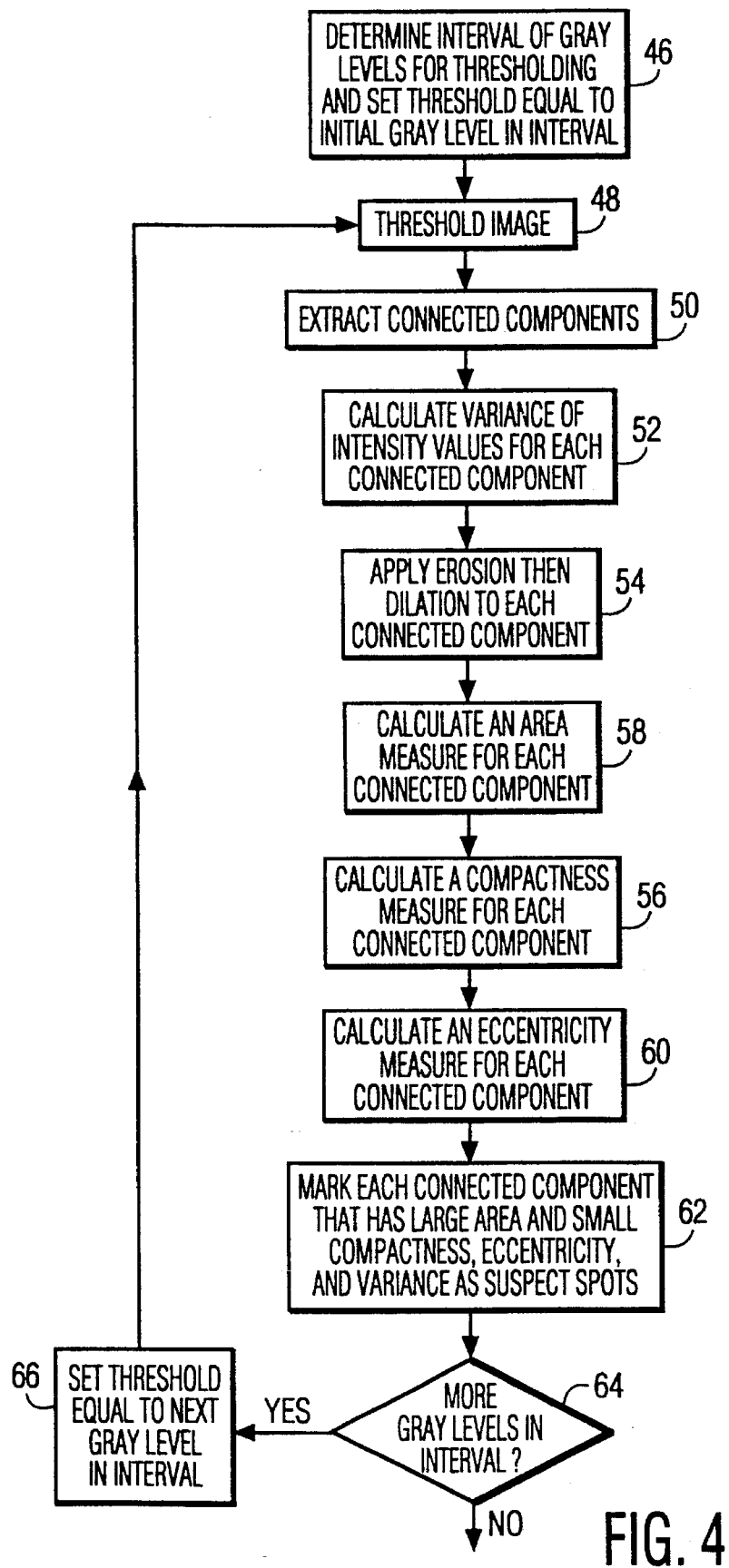
FIG. 4 is a more detailed flow chart of portions shown in the flow chart of FIG. 3 for individually processing mammograms to discriminate spots.

Next in the flow chart of FIG. 4, in step 48 the image is thresholded at the current threshold level to produce a binary image whose pixels having an intensity greater than or equal to the current threshold level are assigned the value one and whose pixels having an intensity less than the current threshold level are assigned the value zero. Alternatively, the thresholded image may be a gray scale image obtained from the background removed image input to step 46, by copying all pixel intensities that are not less than the current threshold level and setting the pixels having an intensity less than the current threshold level to the value zero.

In step 50, spots referred to as "connected components" are extracted from the thresholded image. Each "connected component" is a set of pixels having non-zero values, in which any two pixels of the set are ultimately connected to each other via a run of adjacent pixels in the set. These sets are identified conveniently by the following phases: a) generating a Line-Adjacency Graph (LAG), b) scanning the LAG to determine the number of different connected components (CC's), and c) again scanning the LAG to create a mask image and several summary arrays that define and describe each CC.

The method to create an LAG in phase a) above is based on the description in the book "Algorithms for Graphics and Image Processing" by Pavlidis, Computer Science Press, 1982, pp. 116–120. It consists of for each line of the thresholded image, finding runs of adjacent non-zero valued pixels, comparing the position of the runs on the current and prior adjacent line, and recording any overlap.

Although the LAG specifies which lines overlap, it does not define a connected component. Thus in phase b), each the record of overlapping runs is scanned to determine to which CC each run belongs. Along the way, the total number of connected components is computed.

Once the set of CC's is known, then in phase c) a mask image and several data objects to define each CC are computed. The mask image is essentially the thresholded image in which all non-zero pixels contain the number of the CC to which they belong. The additional data objects include a vector containing the number of pixels in each CC, which is a measure of area, and an array defining a bounding box (minimum and maximum column and row) for each CC.

After the extraction of connected components, in step 52 the variance Var of the intensities of the pixels in each CC is computed separately for each CC in accordance with the following equation:

$$Var = \frac{1}{n} \sum_{i=1}^{n} (g_i - \mu)^2$$

where $g_i$ is the intensity of the ith pixel in the connected region, $\mu$ is the mean value of the intensities of the pixels in the connected region and n is the number of pixels in the connected region. Alternatively, a measure of uniformity might be used, for example, the inverse of the variance.

After, the computation of variance, the connected regions are smoothed in step 54 by erosion and then dilation. Preferably a structure element which is a 3 by 3 matrix of ones is used for each operation. These operations smooth sharp irregularities in the boundaries of the connected regions. Thereafter in step 56, an area measure A for each smoothed CC is computed, conveniently as the number of pixels therein. Then in step 58 a compactness measure Compact is computed for each CC as follows:

$$Compact = \frac{P^2}{A}$$

where P is the perimeter of the connected region and A is its area.

An eccentricity measure Ecc is formed in step 60 as follows:

$$Ecc = \frac{r_{max}}{r_{min}}$$

where $r_{max}$ and $r_{min}$ are the maximum and minimum distances between the center of the connected area and the perimeter.

Then in step 50, the aforementioned measures Compact, Ecc, Var and A (which may be considered as components of a feature vector) are compared with threshold values $T_C$, $T_V$, $T_A$ and $T_A$, respectively for each CC. If Compact, Ecc, and Vat are less than or equal to $T_C$, $T_E$, and $T_V$, respectively and A is greater than or equal to $T_A$, each pixel of the CC is marked as belonging to a candidate suspect CC. After all CC's that were discriminated by the current threshold level are considered, then in step 64, it is tested whether there are more gray levels in the interval. If there are, then in step 66 the current threshold Lev is changed to the next threshold level in order and step 48 is retuned to where the original background removed image is thresholded at the new current threshold level. Steps 48 to 62 are repeated for each threshold level Lev until it is determined at step 64 that there are no more gray levels remaining in the internal.

Values of the thresholds used to test the measures A, Compact, Ecc and Var obtained empirically. The following values thus obtained have given good results with a 256 gray scale 480 by 520 pixel image, in which each pixel represents a square 0.4 mm on a side:

$T_A$=130 pixels
$T_C$=150
$T_E$=2.7
$T_V$=50

In preparation for the comparison or correlation in step 68 (FIG. 3) of the characteristics of the two collections of candidate suspect spots identified in the input arrays 36a, 36b produced from mammogram images taken from different viewing directions, the feature vector for at least the candidate suspect spots is augmented by the components "Dep" and "Lev" corresponding respectively to the depth of the spot relative to the nipple N and the threshold level at which the spot was discriminated, the latter being a convenient measure of the brightness of the spot.

It should be appreciated that the marking of pixels as belonging to a candidate suspect connected area is a cumulative operation. After, all threshold levels in the interval have been applied, then the result is a collection of candidate suspect spots revealed from any of the threshold levels. Consequently, in view of the large number of threshold levels used, in general, groups of at least partially overlapping candidate suspect spots are present in the collection. It is noted that a key aspect of the present invention is that the resolution of these overlaps is postponed until after the aforementioned comparison or correlation in step 68.

The previously determined measures of the candidate suspect spots determined in blocks 44a and 44b and the position reference information determined in blocks 40a and 40b (or alternatively the augmented feature vector containing the components: Compact, Ecc, Var, A, Dep, and Lev) are used by block 66 to form comparative measures of characteristics of each candidate suspect spot S1 identified in the first viewing direction view relative to every candidate suspect spot S2 identified in the second viewing direction. For purposes of clarity and since it does not appear necessary to use Compact at this stage, the relevant measures for spot S1 in the first viewing direction are referred to as Ecc1, Var1, A1, Dep1 and Lev1 and for spot S2 in the second viewing direction are referred to as Ecc2, Var2, A2, Dep2, and Lev2. In particular, absolute values of eccentricity difference ED, variance difference VD, and depth distance DD and area ratio AR and threshold level ratio LR ratio are preferably formed as follows:

$ED = Ecc1 - Ecc2$ $VD = Var1 - Var2$ $DD = Dep1 - Dep2$ $AR = A1/A2$ $LR = Lev1/Lev2$

In step 70, criteria are applied for each comparative measure. Spots in the two views must satisfy each of the criteria in order to be determined as corresponding. Appropriate criteria are the following:

$ED < 1.5$ $VD < 0.1$ $DD < 50$ pixels (i.e. 2 cm)

$0.67 \leq AR \leq 1.5$ $0.67 \leq LR \leq 1.5$

Also in step 70, groups of overlapping spots passing these criteria are resolved by for each group retaining the spot having the largest area A. For the purpose of determining whether a spot is a member of a group of overlapping spots, it is determined whether the center of the spot CS falls within the bounding box of any other spot (a box tangent on all four sides to a spot).

After application of the aforementioned criteria to the comparative measures and the resolution of overlapping spots, in step 32 the resultant corresponding spots as well as the skinline SL and detected nipple N are marked or enhanced in the input arrays 36a and 36b to produce output arrays 34a and 34b. These arrays may be displayed one at a time selectively, or may be assembled into a side by side view.

It should now be appreciated that the objects of the present invention have been satisfied. While the present invention has been described in particular detail, numerous modifications are possible within the intended spirit and scope of the invention. For example, comparison of characteristics of suspect areas identified in mammograms taken from different viewing directions is also two view comparison is also useful for correlating clusters of microcalcifications. The identification of suspect clusters of microcalcifications is described in U.S. patent application, Ser. No. 08/003,071, filed Jan. 11, 1993, entitled "Computer Detection of Microcalcifications in Mammograms", which is also assigned to the same assignee as the present invention.

What is claimed is:

1. A method of producing a computer-enhanced mammogram comprising:

irradiating a breast of a patient being examined with X-ray radiation sequentially in a predetermined first viewing direction and in a predetermined different second viewing direction;

receiving the X-ray radiation exiting the breast sequentially from said first viewing direction and from said second viewing direction within respective two-dimensional fields;

producing digital signals as a function of the X-ray radiation received, which digital signals correspond to a first input two-dimensional array of digital pixels for said first viewing direction and a second input two-dimensional array of digital pixels for said second viewing direction;

in response to said signals, storing said first input two-dimensional array and said second input two-dimensional array in a digital memory means accessible to a computer; and with said computer:

for each of the first input array and the second input array, detecting a skinline and thereby segmenting the array into breast and background regions, identifying a reference point along the detected skinline corresponding to the location of the nipple, and identifying spots within the breast region which based on their size and shape are suspect;

correlating characteristics of spots identified as suspect in the first input array with characteristics of spots identified as suspect in the second input array, said correlating including comparing positions of spots identified as suspect in the first input array relative to the identified reference point in said first input array with the positions of the spots identified as suspect in the second input array relative to the identified reference point in said second input array, and producing an output two-dimensional array of digital pixels from the at least one of the first input array and the second input array in which the spots identified as suspect in at least one of the first input array and the second input array whose characteristics are correlated within predetermined criteria to the spots identified as suspect in the other of the first input array and the second input array are marked or enhanced.

2. The method as claimed in claim 1, wherein said comparing positions of the spots identified as suspect in the first input array with the positions of the spots identified as suspect in the second input array is by comparing depths relative to the reference point along a line passing through the reference point and a center of mass of the breast region.

3. The method as claimed in claim 1, wherein said identifying of spots within the breast region as suspect based on their size and shape comprises thresholding at least a portion of the stored input array at, at least, 20 different threshold levels to discriminate spots, for each spot discriminated, forming a plurality of measures of said spot, including of its size and shape, and determining whether the formed plurality of measures fall within further predetermined criteria.

4. The method as claimed in claim 2, wherein said identifying of spots within the breast region as suspect based on their size and shape comprises thresholding at least a portion of the stored input array at, at least, 20 different threshold levels to discriminate spots, for each spot discriminated, forming a plurality of measures of said spot, including of its size and shape, and determining whether the formed plurality of measures fall within predetermined criteria.

5. The method as claimed in claim 3, wherein after said correlating, if there are any groups of overlapping spots identified as suspect in the at least one of the first input array and the second input array whose characteristics are correlated with spots identified as suspect in the other of the first input array and the second input array within said predetermined criteria, then with respect to said groups of overlapping spots, only the largest spot of each such group is marked or enhanced.

6. The method as claimed in claim 3, wherein said formed measures include one of the variance or uniformity of values of the digital pixels comprising said spot.

7. The method as claimed in claim 4, wherein said formed measures include one of the variance or uniformity of values of the digital pixels comprising said spot.

8. The method as claimed in claim 3, wherein said correlating of characteristics includes comparison of the thresholds at which the spots were discriminated.

9. The method as claimed in claim 4, wherein said correlating of characteristics includes comparison of the thresholds at which the spots were discriminated.

10. A system for producing a computer-enhanced mammogram comprising:

means including an X-ray source, for irradiating a breast of a patient under examination with X-ray radiation sequentially in predetermined first and second different viewing directions;

means for receiving the X-ray radiation exiting the breast sequentially from said first and second viewing directions within respective two-dimensional fields;

means for producing digital signals as a function of the X-ray radiation received, which digital signals correspond to first and second input two-dimensional arrays of digital pixels for the respective first and second viewing directions;

a computer;

a digital memory means accessible to said computer;

means for, in response to said signals, storing said input two-dimensional array of digital pixels in said digital memory means; and display means responsive to said computer for displaying an output array of digital pixels produced by said computer as an image;

wherein said computer is configured for:

processing the stored first and second input two-dimensional arrays of digital pixels by for each of the first input array and the second input array, detecting the skinline and thereby segmenting the array into breast and background regions, identifying a reference point along the skinline corresponding to the location of the nipple, and identifying spots within the breast region which based on their size and shape are suspect;

correlating characteristics of spots identified as suspect in the first input array with characteristics of spots identified as suspect masses in the second input array, said correlating including comparing positions of spots identified as suspect in the first input array relative to the identified reference point c in said first input array with the positions of the spots identified as suspect in the second input array relative to the identified reference point in said second input array, and producing the output two-dimensional array of digital pixels from the at least one of the first input array and the second input array in which any spots identified as suspect in at least one of the first input array and the second input array whose characteristics are correlated within predetermined criteria to the spots identified as suspect in the other of the first input array and the second input array are marked or enhanced.

11. The apparatus as claimed in claim 10, wherein said identifying of spots within the breast region as suspect based on their size and shape comprises thresholding at least a portion of the stored input array at, at least, 20 different threshold levels to discriminate spots, for each spot discriminated, forming a plurality of measures of said spot, including of its size and shape, and determining whether the formed plurality of measures fall within further predetermined criteria.

12. The apparatus as claimed in claim 11, wherein after said correlating, if there are any groups of overlapping spots identified as suspect in the at least one of the first input array and the second input array whose characteristics are correlated with spots identified as suspect in the other of the first input array and the second input array within said predetermined criteria, then with respect to said groups of overlapping spots, only the largest spot of each such group is marked or enhanced.

13. The apparatus as claimed in claim 11, wherein said formed measures include one of the variance or uniformity of values of the digital pixels comprising said spot.

14. The apparatus as claimed in claim 11, wherein said correlating of characteristics includes comparison of the thresholds at which the spots were discriminated.

15. The apparatus as claimed in claim 10, wherein said comparing positions of the spots identified as suspect in the first input array with the positions of the spots identified as suspect in the second input array is by comparing depths relative to the reference point along a line passing through the reference point and a center of mass of the breast region.

16. The apparatus as claimed in claim 15, wherein said identifying of spots within the breast region as suspect based on their size and shape comprises thresholding at least a portion of the stored input array at, at least, 20 different threshold levels to discriminate spots, for each spot discriminated, forming a plurality of measures of said spot, including of its size and shape, and determining whether the formed plurality of measures fall within predetermined criteria.

17. The apparatus as claimed in claim 16, wherein said formed measures include one of the variance or uniformity of values of the digital pixels comprising said spot.

18. The apparatus as claimed in claim 16, wherein said correlating of characteristics includes comparison of the thresholds at which the spots were discriminated.

* * * * *